(12) United States Patent
Reschke

(10) Patent No.: US 8,679,115 B2
(45) Date of Patent: Mar. 25, 2014

(54) ELECTRICAL CUTTING AND VESSEL SEALING JAW MEMBERS

(75) Inventor: Arlan J. Reschke, Longmont, CO (US)

(73) Assignee: Covidien LP, Mansfield, MA (US)

( * ) Notice: Subject to any disclaimer, the term of this patent is extended or adjusted under 35 U.S.C. 154(b) by 669 days.

(21) Appl. No.: 12/543,831

(22) Filed: Aug. 19, 2009

(65) Prior Publication Data

US 2011/0046623 A1 Feb. 24, 2011

(51) Int. Cl.
*A61B 18/18* (2006.01)
*A61B 17/32* (2006.01)

(52) U.S. Cl.
USPC .............. 606/52; 606/41; 606/50; 606/205

(58) Field of Classification Search
USPC ................. 606/41–45, 50–52, 205–209
See application file for complete search history.

(56) References Cited

U.S. PATENT DOCUMENTS

| | | | | |
|---|---|---|---|---|
| 5,456,684 | A * | 10/1995 | Schmidt et al. | 606/41 |
| 5,624,452 | A * | 4/1997 | Yates | 606/139 |
| 6,024,744 | A | 2/2000 | Kese et al. | |
| 6,736,813 | B2 | 5/2004 | Yamauchi et al. | |
| 6,790,217 | B2 * | 9/2004 | Schulze et al. | 606/171 |
| 6,821,273 | B2 * | 11/2004 | Mollenauer | 606/28 |
| 6,953,461 | B2 | 10/2005 | McClurken et al. | |
| 7,276,068 | B2 | 10/2007 | Johnson et al. | |
| 7,445,621 | B2 | 11/2008 | Dumbauld et al. | |
| 2002/0049442 | A1 | 4/2002 | Roberts et al. | |
| 2004/0078035 | A1 | 4/2004 | Kanehira et al. | |
| 2005/0033278 | A1 | 2/2005 | Mcclurken et al. | |
| 2008/0039835 | A1 * | 2/2008 | Johnson et al. | 606/48 |
| 2008/0195093 | A1 | 8/2008 | Couture et al. | |

FOREIGN PATENT DOCUMENTS

| | | |
|---|---|---|
| CA | 2104423 | 2/1994 |
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |

(Continued)

OTHER PUBLICATIONS

U.S. Appl. No. 12/336,970, filed Dec. 17, 2008.

(Continued)

*Primary Examiner* — Linda Dvorak
*Assistant Examiner* — Brian M Antiskay

(57) ABSTRACT

The present disclosure relates to an end effector assembly for use with an electrosurgical instrument. The end effector assembly includes a pair of opposing first and second jaw members and a first electrically conductive cutting plate. The pair of opposing first and second jaw members is movable to cooperatively grasp tissue. Each of the jaw members includes a tissue contacting plate that is disposed thereon and has a longitudinal channel that is defined therealong. The first electrically conductive cutting plate includes a cutting element that extends along the first electrically conductive cutting plate and into the longitudinal channel of the first jaw member to engage and electrosurgically sever tissue upon activation thereof.

15 Claims, 7 Drawing Sheets

(56) References Cited

FOREIGN PATENT DOCUMENTS

| | | |
|---|---|---|
| DE | 19738457 | 1/2009 |
| EP | 1159926 | 12/2001 |
| EP | 1632192 | 3/2006 |
| GB | 623316 | 5/1949 |
| GB | 1490585 | 11/1977 |
| GB | 2214430 A | 6/1989 |
| GB | 2213416 A | 8/1989 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 97/24073 | 7/1997 |

OTHER PUBLICATIONS

U.S. Appl. No. 12/399,614, filed Mar. 6, 2009.
U.S. Appl. No. 12/195,624, filed Aug. 21, 2008.
U.S. Appl. No. 12/367,791, filed Feb. 9, 2009.
U.S. Appl. No. 12/361,367, filed Jan. 28, 2009.
U.S. Appl. No. 12/361,375, filed Jan. 28, 2009.
U.S. Appl. No. 12/400,901, filed Mar. 10, 2009.
U.S. Appl. No. 12/176,679, filed Jul. 21, 2008.
U.S. Appl. No. 12/237,515, filed Sep. 25, 2008.
U.S. Appl. No. 12/204,976, filed Sep. 5, 2008.
U.S. Appl. No. 12/192,170, filed Aug. 15, 2008.
U.S. Appl. No. 12/233,157, filed Sep. 18, 2008.
U.S. Appl. No. 12/237,582, filed Sep. 25, 2008.
U.S. Appl. No. 12/210,598, filed Sep. 15, 2008.
U.S. Appl. No. 12/200,154, filed Aug. 28, 2008.
U.S. Appl. No. 12/211,205, filed Sep. 16, 2008.
U.S. Appl. No. 12/244,873, filed Oct. 3, 2008.
U.S. Appl. No. 12/246,553, filed Oct. 7, 2008.
U.S. Appl. No. 12/248,115, filed Oct. 9, 2008.
U.S. Appl. No. 12/353,474, filed Jan. 14, 2009.
U.S. Appl. No. 12/353,470, filed Jan. 14, 2009.
U.S. Appl. No. 12/352,942, filed Jan. 13, 2009.
U.S. Appl. No. 12/237,556, filed Sep. 25, 2008.
U.S. Appl. No. 12/411,542, filed Mar. 26, 2009.
U.S. Appl. No. 12/248,104, filed Oct. 9, 2008.
U.S. Appl. No. 12/254,123, filed Oct. 20, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/236,666, filed Sep. 24, 2008.
U.S. Appl. No. 12/192,189, filed Aug. 15, 2008.
U.S. Appl. No. 12/192,243, filed Aug. 15, 2008.
U.S. Appl. No. 12/331,643, filed Dec. 10, 2008.
U.S. Appl. No. 12/353,466, filed Jan. 14, 2009.
U.S. Appl. No. 12/363,086, filed Jan. 30, 2009.
U.S. Appl. No. 12/419,729, filed Apr. 7, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.

(56) References Cited

OTHER PUBLICATIONS

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.

* cited by examiner

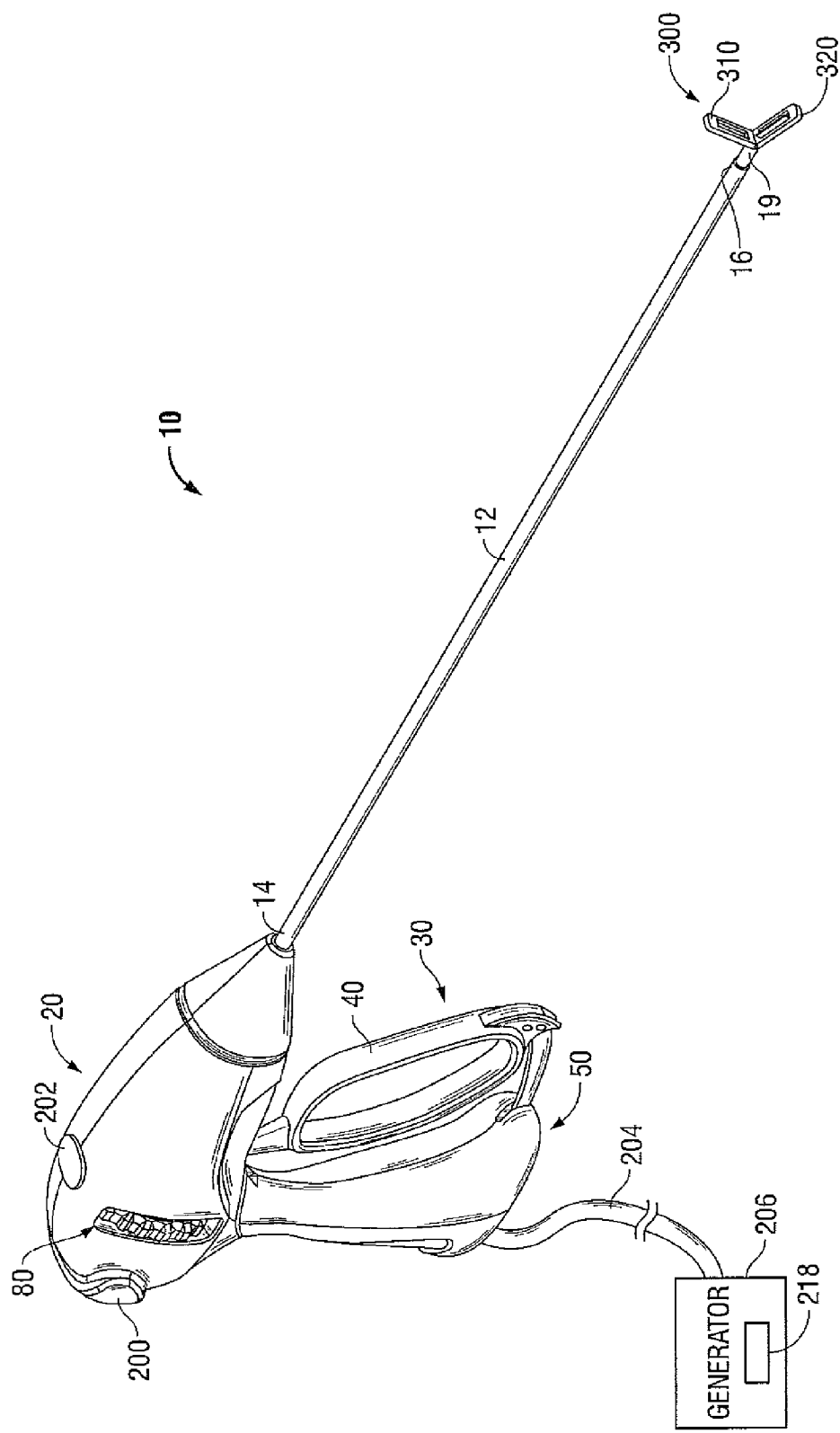

ELECTRICAL CUTTING AND VESSEL SEALING JAW MEMBERS

BACKGROUND

1. Technical Field

The present disclosure relates to an apparatus that includes an end effector assembly for performing electrosurgical procedures, and, more particularly, an end effector assembly that allows a user to selectively seal and cut tissue.

2. Description of Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can cauterize, coagulate/desiccate, and/or simply reduce or slow the bleeding, by controlling the intensity, frequency and duration of the electrosurgical energy applied between the electrodes and through the tissue.

Typically, and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. This additional step may be both time consuming (particularly when sealing a significant number of vessels) and may contribute to imprecise separation of the tissue along the sealing line due to the misalignment or misplacement of the severing instrument along the center of the tissue seal.

Certain types of open and endoscopic electrosurgical forceps, as mentioned above, also utilize a movable knife or cutting blade that is movable via a knife channel. The knife channel is defined by a jaw member and is often characterized as a narrow cavity within the jaw member. After tissue has been treated (e.g., sealed or coagulated) by the forceps, the knife is moved along the knife channel and cuts or severs the treated tissue. In certain situations, tissue debris is trapped within the knife channel and frequently obstructs the path of the knife. When this or similar situations occur, unnecessary complications arise for the user during a surgical procedure.

SUMMARY

The present disclosure relates to an end effector assembly for use with an electrosurgical instrument. The end effector assembly includes a pair of opposing first and second jaw members and a first electrically conductive cutting plate. The pair of opposing first and second jaw members is movable to cooperatively grasp tissue. Each of the jaw members includes a tissue contacting plate that is disposed thereon and has a longitudinal channel that is defined therealong. The longitudinal channels are disposed in substantial vertical registration relative to one another. The first electrically conductive cutting plate is disposed on the first jaw member below the tissue contacting plate and is adapted to connect to a first potential of an electrosurgical energy source. The first electrically conductive cutting plate includes a cutting element that extends along the first electrically conductive cutting plate and into the longitudinal channel of the first jaw member to engage and electrosurgically sever tissue upon activation thereof. The cutting element may include a cutting edge that facilitates mechanical separation of tissue during electrical activation thereof. The first electrically conductive cutting plate may include a stamped portion that is bent therefrom to form the cutting element.

In embodiments, the tissue contacting plate of the first jaw member may be electrically non-conductive or electrically conductive and adapted to connect to the electrosurgical energy source. The first jaw member also may include an insulator that is disposed between the tissue contacting plate and the first electrically conductive cutting plate. A portion of the electrically conductive cutting plate of the first jaw member may be sandwiched between two layers of insulative material.

In embodiments, the second jaw member may include a second electrically conductive cutting plate that is disposed on a non-tissue contacting side of the tissue contacting plate. The second electrically conductive cutting plate of the second jaw member may be adapted to connect to an opposite potential of an electrosurgical energy source. A portion of the second electrically conductive cutting plate may be disposed within the longitudinal channel of the tissue contacting plate of the second jaw member. Additionally or alternatively, a portion of the electrically conductive cutting plates of the jaw members may be sandwiched between two layers of insulative material, for example, a polymeric material.

In embodiments, the cutting element of the first electrically conductive cutting plate and the second electrically conductive cutting plate cooperate to grasp tissue therebetween. In embodiments, the cutting element of the first electrically conductive cutting plate may be centrally or non-centrally disposed within the longitudinal channel of the at least the first jaw member.

The present disclosure also relates to an end effector assembly for use with an electrosurgical instrument and includes a pair of opposing first and second jaw members and a first electrically resistive cutting plate. The pair of opposing first and second jaw members is movable to cooperatively grasp tissue. Each of the jaw members includes a tissue contacting plate that is disposed thereon and has a longitudinal channel defined therealong. The longitudinal channels are disposed in substantial vertical registration relative to one another. The first electrically resistive cutting plate is disposed on the first jaw member below the tissue contacting plate and is adapted to connect to an electrical energy source. The first electrically resistive cutting plate includes a cutting element that extends along the first electrically resistive cutting plate and into the longitudinal channel of the first jaw member to engage, heat, and separate tissue upon activation thereof. The first electrically resistive cutting plate may be configured to heat tissue to a threshold temperature assuring separation of tissue.

The present disclosure also relates to a method of manufacturing an end effector assembly. The method includes the step of providing a pair of opposing first and second jaw members that is movable to cooperatively grasp tissue. Each of the jaw members include a tissue contacting plate that is disposed thereon and has a longitudinal channel that is defined therealong. The longitudinal channels are disposed in substantial vertical registration relative to one another, respectively. The first electrically conductive cutting plate is adapted to connect to a first potential of an electrosurgical energy source. The method also includes the step of providing a first electrically conductive cutting plate disposing on the first jaw member below the tissue contacting plate. The method also includes the step of stamping the first electrically conductive cutting plate to define a cutting element. The method also includes the step of bending the cutting element about a bending region such that the cutting element extends along the first electrically conductive cutting plate and into the longitudinal channel of the at least the first jaw member.

The method also includes the step of applying an insulative material to a portion of the first electrically conductive cutting plate.

BRIEF DESCRIPTION OF THE DRAWINGS

Various embodiments of the subject instrument are described herein with reference to the drawings wherein:

FIG. 1 is a perspective view of an endoscopic bipolar forceps having an end effector assembly attached to a distal end of the forceps according to one embodiment of the present disclosure;

DETAILED DESCRIPTION

Figure 2A:
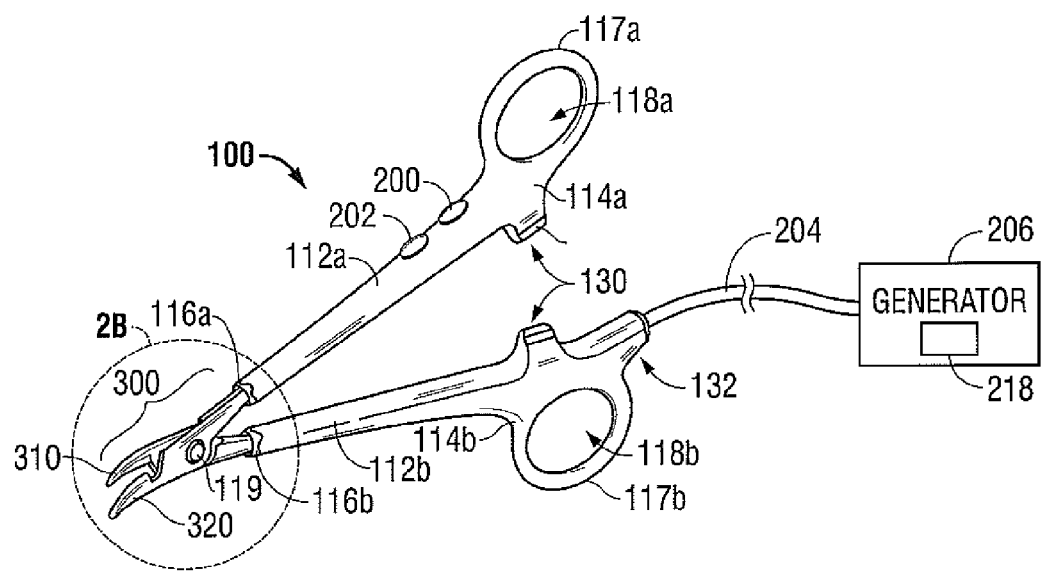
FIG. 2A is a perspective view of an open bipolar forceps having a pair of first and second shafts and further having an end effector assembly attached to a distal end of the shafts according to one embodiment of the present disclosure.

Embodiments of the presently disclosed electrosurgical instrument are described in detail with reference to the drawing figures wherein like reference numerals identify similar or identical elements. As used herein, the term "distal" refers to that portion which is further from a user while the term "proximal" refers to that portion which is closer to a user.

Referring now to the figures, FIG. 1 depicts a bipolar forceps 10 as used in correlation with endoscopic surgical procedures and FIG. 2A depicts an open forceps 100 as used in correlation with open surgical procedures. For the purposes herein, either an endoscopic instrument or an open instrument may be utilized with the novel end effector assembly described herein. It should be noted that different electrical and mechanical connections and considerations apply to each particular type of instrument. However, the novel aspects, with respect to the end effector assembly and its operating characteristics, remain generally consistent with respect to both the endoscopic or open designs.

Figure 4:
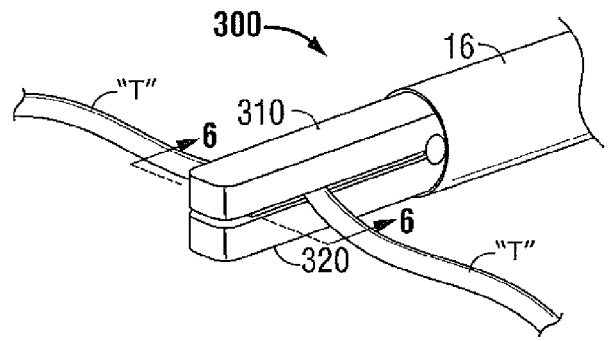
FIG. 4 is a perspective view of the end effector assembly of FIG. 3A shown in a closed position and grasping tissue therebetween.

Turning now to FIG. 1, a bipolar forceps 10 is shown for use with various endoscopic surgical procedures and generally includes a housing 20, a handle assembly 30, a rotating assembly 80, first and second switch assemblies 200 and 202, respectively, and an end effector assembly 300. The end effector assembly 300 includes opposing jaw members 310 and 320 that mutually cooperate to grasp, seal and/or divide tubular vessels/vascular tissue, or any other suitable tissue (as shown in FIG. 4). The opposing jaw members 310 and 320 include sealing plates 312 and 322 (also referred to, throughout the description, as sealing plates, sealing electrodes, or tissue contacting plates) and cutting plates 316 and 330 (also referred to, throughout the description, as electrically conductive cutting plates or cutting electrodes), which will be further described below Forceps 10 includes a shaft 12 that has a distal end 16 dimensioned to mechanically engage the end effector assembly 300 and a proximal end 14 that mechanically engages the housing 20. The shaft 12 may include one or more known mechanically engaging components that are designed to securely receive and engage the end effector assembly 300 such that the jaw members 310 and 320 are pivotable relative to one another to engage and grasp tissue therebetween.

The proximal end 14 of the shaft 12 mechanically engages the rotating assembly 80 (not shown) to facilitate rotation of the end effector assembly 300. Handle assembly 30 includes a fixed handle 50 and a movable handle 40. Fixed handle 50 is integrally associated with housing 20 and handle 40 is movable relative to fixed handle 50 to actuate the opposing jaw members 310 and 320 of the end effector assembly 300.

First and second switch assemblies 200 and 202 are configured to selectively provide electrical energy to the end effector assembly 300. More particularly, the first switch assembly 200 is configured to selectively provide electrical energy to the sealing plates 312, 322 and second switch assembly 202 is configured to selectively provide electrical energy to cutting plates 316, 330 (as shown in the various figures). Handle assembly 30 further includes a cable 204 that connects the forceps 10 to a source of electrosurgical energy, e.g., an electrosurgical generator 206. Cable 204 is internally divided within the handle assembly 30 and the shaft 12 to transport electrosurgical energy through various conductive paths and ultimately to end effector assembly 300.

First and second switch assemblies 200 and 202 may also cooperate with a smart sensor 218 (or smart circuit, computer, feedback loop, etc.) that automatically triggers one of the switches to change between the "sealing" mode and the "cutting" mode upon the satisfaction of a particular parameter. For example, the smart sensor 218 may include a feedback loop that indicates when a tissue seal is complete based upon one or more of the following parameters: tissue temperature, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal. A separate lead may be connected between the smart sensor and the generator for visual and/or audible feedback purposes.

Alternatively, the smart sensor 218 may be configured to activate based upon a desired cutting parameter and/or after an effective seal is created or has been verified. For example, after effectively sealing the tissue, the cutting plate(s) may be automatically activated based upon a desired end tissue thickness at the seal.

As mentioned above, the end effector assembly 300 is positioned on the distal end 16 of shaft 12 and includes the opposing jaw members 310 and 320. Movable handle 40 of the handle assembly 30 translates movement of the jaw members 310 and 320 from an open position (also referred to as a first position), such that the jaw members 310 and 320 are disposed in spaced relation relative to one another to a clamped or closed position (also referred to as a second position), such that the jaw members 310 and 320 cooperate to grasp tissue therebetween.

Figure 2B:
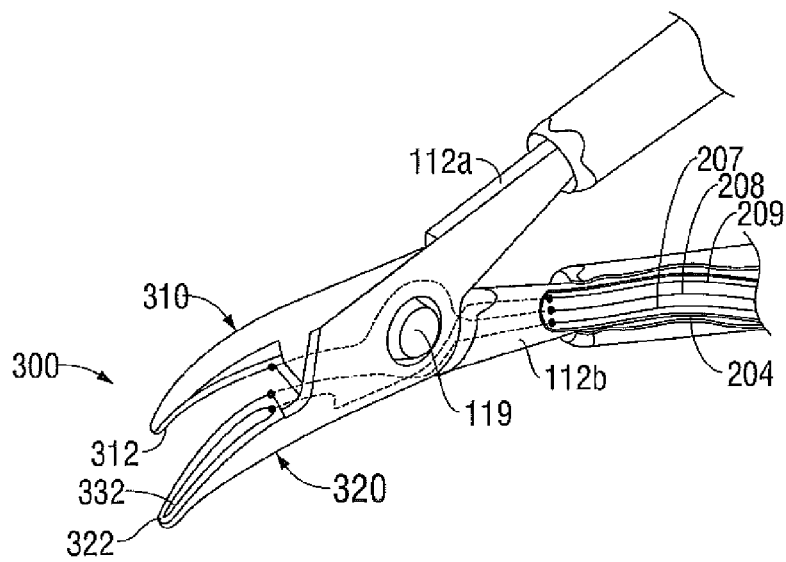
FIG. 2B is an enlarged schematic view of the end effector assembly of FIG. 2A.

Referring now to FIGS. 2A and 2B, an open forceps 100 is depicted and includes end effector assembly 300 (similar to forceps 10) that is attached to a pair of elongated shaft portions 112a and 112b. Each elongated shaft portion, 112a and 112b, respectively, has a proximal end 114a and 114b, respectively, and a distal end 116a and 116b, respectively. The end effector assembly 300 includes jaw members 310 and 320 that attach to distal ends 116a and 116b of shafts 112a and 112b, respectively. The jaw members 310 and 320 are connected about pivot pin 119 that allows the jaw members 310 and 320 to pivot relative to one another from the first to second positions for treating tissue (as described above). Seal plates 312 and 322 are connected to opposing jaw members 310 and 320 and include electrical connections through or around the pivot pin 119.

Each shaft 112a and 112b includes a handle 117a and 117b disposed at the proximal end 114a and 114b thereof. Handles 117a and 117b facilitate movement of the shafts 112a and 112b relative to one another which, in turn, pivot the jaw members 310 and 320 from the open position wherein the jaw members 310 and 320 are disposed in spaced relation relative to one another to the clamping or closed position wherein the jaw members 310 and 320 cooperate to grasp tissue therebetween.

In some embodiments, one or more of the shafts, e.g., shaft 112a, includes a first switch assembly 200 and a second switch assembly 202. First and second switch assemblies 200 and 202 are configured to selectively provide electrical energy to the end effector assembly 300. More particularly, the first switch assembly 200 is configured to selectively provide electrical energy to the sealing plates 312, 322 and a second switch assembly 202 is configured to selectively provide electrical energy to cutting plates 316, 330 (as shown in the various figures).

In an example embodiment, as depicted in FIG. 2A, a ratchet 130 is included for selectively locking the jaw members 310 and 320 relative to one another at various positions during pivoting. The ratchet 130 includes a first mechanical interface 130a associated with shaft 112a and a second mating mechanical interface 130b associated with shaft 112b. Each position associated with the cooperating ratchet interfaces 130a and 130b holds a specific, i.e., constant strain energy in the shaft members 112a and 112b which, in turn, transmits a specific closing force to the jaw members 310 and 320. It is envisioned that the ratchet 130 may include graduations or other visual markings that enable the user to easily and quickly ascertain and control the amount of closure force desired between the jaw members 310 and 320.

With continued reference to FIG. 2A, forceps 100 is depicted having a cable 204 that connects the forceps 100 to a source of electrosurgical energy, e.g., an electrosurgical generator 206. In a similar fashion to forceps 10, cable 204 of forceps 100 is internally divided within the shaft 112b to transmit electrosurgical energy through various electrical conductive paths to the components of the end effector assembly 300.

As best shown in the example schematic illustration of FIG. 2B, the jaw members 310 and 320 of both the endoscopic version of FIG. 1 and the open version of FIG. 2A are generally symmetrical and include similar component features that cooperate to permit facile rotation about pivots 19, 119 to effect the grasping, sealing and/or cutting of tissue. Each jaw member 310 and 320 includes an electrically conductive tissue contacting surface 312 and 322, respectively, which cooperate to engage the tissue during sealing and/or cutting. Further, each jaw members 310 and 320 includes an electrically energizable cutting plate 316 and 330, which cooperate to engage the tissue during sealing and/or cutting. Together, and as shown in the various figures described throughout the description, the end effector assembly 300 includes the combination of the sealing plates 312 and 322 and the cutting plates 316 and 330 to perform various electrosurgical procedures.

Various electrical connections of the end effector assembly 300 may be utilized and can be configured to provide electrical continuity to the sealing plates 312 and 322 and the cutting plates 316 and 330 through the end effector assembly 300. For example, the cable 204 may be configured to contain one or more different wires (e.g., wires 207, 208 and 209) each of which may be configured to carry different electrical potentials. The wires 207, 208 and 209 may be disposed within shaft 112b and connect to various electrical connectors (not shown) disposed within the proximal end of the jaw member 310, which ultimately connect to the electrically conductive sealing plates 312 and 322 and cutting plates 316 and 330.

The various electrical connections contained within cable 204 are typically dielectrically insulated from one another to allow selective and independent activation of either the sealing plates 312, 322 or the cutting plates 316, 330 by any of the first and second switch assemblies 200 and 202. Alternatively, the end effector assembly 300 may include a single connector that includes an internal switch (not shown) to allow selective and independent activation of the sealing plates 312, 322 and the cutting plates 316, 330. The wires 207, 208 and 209 (and/or conductive pathways) do not encumber the movement of the jaw members 310, 320 relative to one another during the manipulation and grasping of tissue. Likewise, the movement of the jaw members 310, 320 does not unnecessarily strain the lead connections.

Turning now to FIGS. 3-9, the present disclosure describes various embodiments of an end effector assembly having electrically conductive cutting plates. FIG. 3A shows the end effector assembly 300 positioned and attached on the distal end 16 of the instrument 10. In general, jaw members 310, 320 include sealing plates 312, 322, cutting plates 316, 330, and first and second insulating materials 314a, 314b and 324a, 324b (shown in FIGS. 7-9). The first and second insulating materials 314a, 314b and 324a, 324b are configured to electrically isolate the cutting plates to prevent any short-circuiting with surrounding elements (e.g., sealing plates 312 and 322).

As depicted in the figures, the seal plates 312, 314 are disposed along the length of the jaw members 310, 320 and are adapted to connect to an electrosurgical generator 206 (shown in FIGS. 1 and 2A) via the various electrical connections described above. Similarly, cutting plates 316 and 330 are also disposed along the length of the jaw members 310, 320 and are adapted to connect to an electrosurgical generator 206. In essence, the cutting plates and the seal plates are parallel to each other and separated via insulating materials, along the jaw members. The seal plates 312, 314 and the cutting plates 316, 330 may be manufactured from any suitable metal, for example, but not limited to, stainless steel. The seal plates 312 and 314 may be press-formed by a stamping process, an overmolding process, a process that involves overmolding a stamped electrically conductive sealing plate, and/or a process that involves overmolding a metal injection molded seal plate.

Figure 3A:
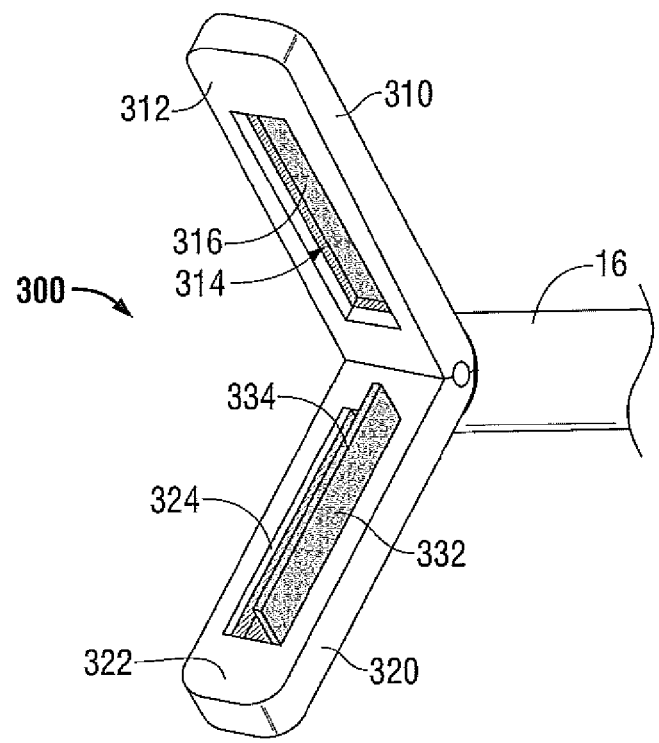
FIG. 3A is a perspective view of the end effector assembly of FIG. 1 illustrating a cutting plate in accordance with an embodiment of the present disclosure.
Figure 3B:
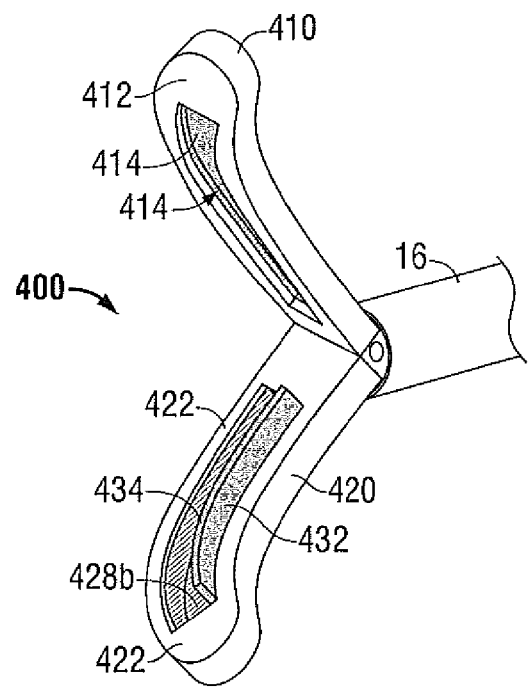
FIG. 3B is a perspective view of another embodiment of the presently disclosed end effector assembly having a curved configuration and shown in an open position having a curved cutting plate in accordance with an embodiment of the present disclosure.

The cutting plates 316 and 330 of the present disclosure may be may be fabricated in a variety of forms. In this manner, the cutting plates are configured and dimensioned to be mounted into customary straight jaw members 310 and 320 (as shown in FIG. 3A), curved jaw members 410 and 420 (as shown in FIG. 3B), or any other shaped jaw members including irregularly shaped jaw members. A novel aspect of the presently disclosed cutting plates is the reduction of movable parts. In essence, cutting plates 330, 430, and 530, as they will all be described further below, are stationary cutting plates that are energized via any suitable type of energy (e.g., electrical, ultrasonic, microwave, cryogenic, heat, and laser).

Figure 6:
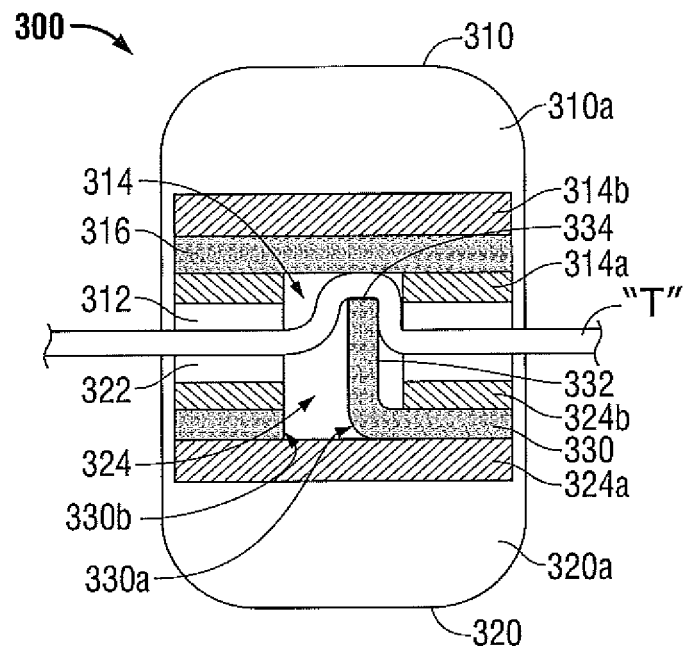
FIG. 6 is a front cross-sectional view of the end effector assembly of FIG. 4.

In an example embodiment, cutting plate 316 is formed in a generally flat-shaped configuration. Cutting plate 330 is press-stamped by any suitable pressing process such that a cutting element or cutting flange 332 is formed about a bending region 330a (as shown in FIG. 6). During use, cutting plate 316 is approximated towards cutting plate 330 such that cutting edge 334 is proximate the cutting plate 316. In some electrosurgical embodiments, cutting plate 316 may be configured to be a ground, while cutting plate 330 may be configured to have an electrical charge, for example, a positive or negative charge, or vice versa. In alternative embodiments, cutting plate 316 may be configured to have a negative charge, while cutting plate 330 may be configured to have a positive charge, or vice versa.

Figure 5A:
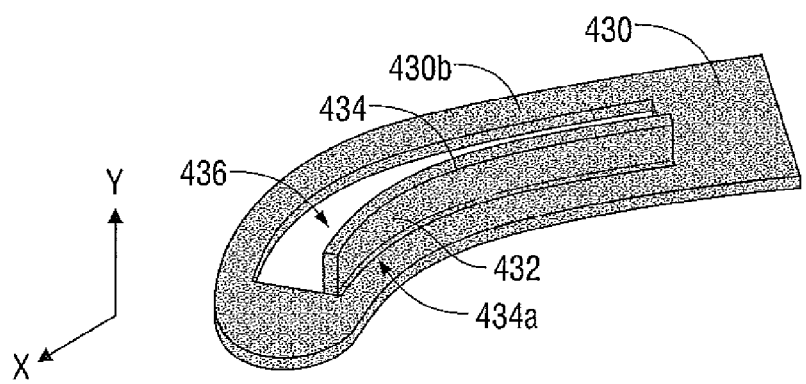
FIG. 5A is a perspective view illustrating the curved cutting plate of FIG. 3B.
Figure 5B:
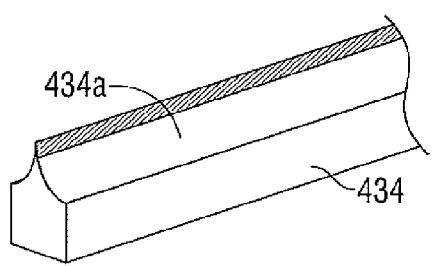
FIG. 5B is a perspective view of an embodiment of a cutting edge of a cutting plate similar to FIG. 3A.
Figure 5C:
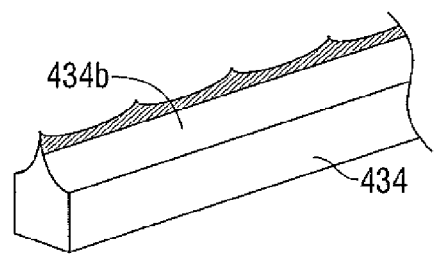
FIG. 5C is a perspective view of another embodiment of a cutting edge of a cutting plate similar to FIG. 3A.

Turning now to another example embodiment, as depicted in FIG. 5A, a curved cutting plate 430 is pressed and/or stamped in such a manner that a cutting flange 432 is formed about a bending region 430a of the cutting plate 430. More specifically, a cut portion 430b of the cutting plate 430 is cut and/or pressed through the sheet of metal and the remaining bent portion 430a is bent to define the cutting flange 432. After cutting plate 430 is pressed or stamped, cutting flange 432 is bent to a substantially normal (e.g., about 90 degrees) configuration, depicted by directional arrow "Y", to a plane of the cutting plate 430, depicted by directional arrow "X." The "hole" created by the press-stamped and/or cutting process of the cutting flange 432 defines an opening 436. A method of manufacturing jaw members 310 and 320 is described hereinbelow in further detail.

In the embodiments depicted by FIGS. 3-5A, the cutting flange 432 includes a substantially dull edge 434 and is configured to cut tissue exclusively via selective electrical activation. However, in other embodiments, as depicted in FIGS. 5B and 5C, cutting flange 434 defines a sharp edge 434a such that the sharpness of edge 434a facilitates cutting of tissue T. It is contemplated that the cutting effect of sharp edge 434a, in combination with the electrosurgical activation of cutting plate 430, will facilitate effective cutting of tissue when grasped between the jaw members 310 and 320. In FIG. 5C, the cutting edge 434 defines a perforated edge 434b (e.g., teeth, serrations, and indentations) that is configured to facilitate grasping and cutting of tissue when held between the jaw members 310 and 320.

Referring now to FIG. 6, the tissue contacting plates or seal plates 312, 322, the cutting plates 316, 330 and, the first and second insulating materials 314a, 314b and 324a, 324b, together, define channels 314 and 324 such that the cutting element 332 of cutting plate 330 can pass therethrough. In this manner, the channels 314 and 324 facilitate the ability of cutting flange 332 to grasp tissue T within the channel 314 and 324 as the jaw members 310 and 320 are approximated to a closed position. As mentioned above, first and second insulating materials 314a, 314b and 324a, 324b, of each respective jaw member, are configured to prevent short-circuiting from occurring between the cutting plates and the seal plates. Additionally or alternatively, the seal plates 312, 322 and the cutting plates 316, 330 may have an insulative material (not explicitly shown) applied thereon. First and second insulating materials 314a, 314b and 324a, 324b are formed from any suitable dielectric material, for example, but not limited to, polymeric materials such as polyvinyl chloride (PVC).

Figure 7:
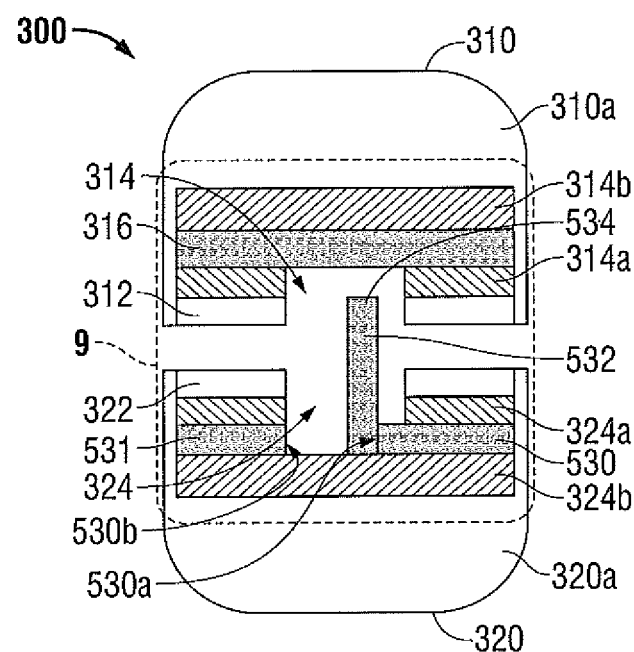
FIG. 7 is a front cross-sectional view of an end effector assembly illustrating another embodiment of a cutting plate in accordance with the present disclosure.

Referring now to FIG. 7, which depicts another example embodiment, jaw member 320 is depicted having a first cutting plate 530 that includes a base portion 531 and a cutting plate portion 532. The cutting flange portion 532 may be fixedly attached to the base portion 531 by any suitable attaching techniques. For example, the cutting flange 532 may be attached by a technique which includes, but not limited to, welding, brazing, adhesive bonding, gluing, or any other suitable attaching process. In this embodiment, the cutting flange 532 is shaped and/or cut to any desired length, width, and/or dimension, to facilitate grasping of tissue T, when the jaw members 310 and 330 are approximated towards the second cutting plate 516 of the opposing jaw member 310.

Figure 8:
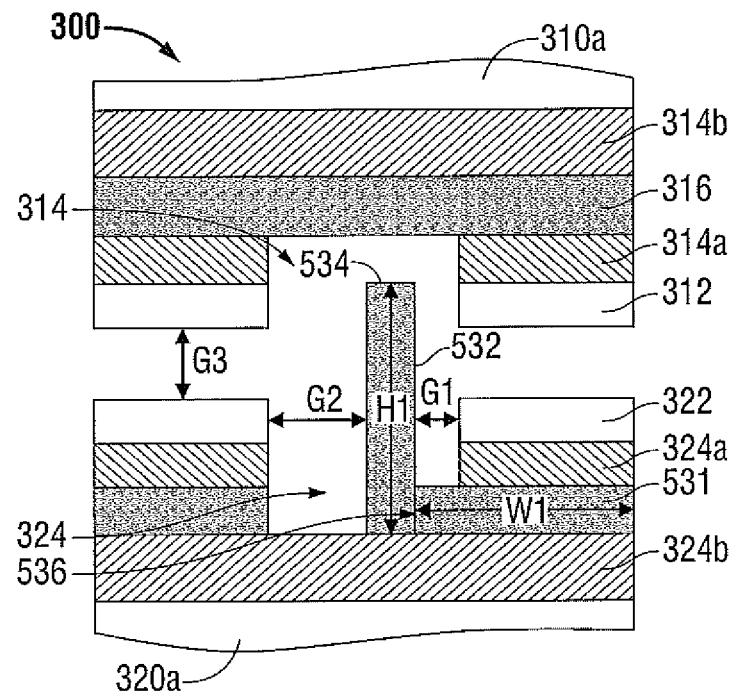
FIG. 8 is a detailed view of the front cross-sectional view of the end effector assembly of FIG. 7.

More particularly, as best shown in FIG. 8, the base portion 531 and the cutting flange 532 are shaped and cut into any configuration in order to define a variety of gaps within the end effector assembly 300. For example, a width W1 of base portion 531 is varied to define gaps G1 and G2. Gaps G1 and G2 define a space between the flange portion 532 and insulating materials 324a within the channel 324. By varying the width W1 of the base portion 531, gaps G1 and G2 are varied such that the flange portion 532 may be moved along the width of channel 324. That is, the flange portion 532 may be centrally or non-centrally disposed within the longitudinal channel 324. Further, a height H1 of flange portion 532 may be varied to define a gap G3 between the opposing seal plates 312 and 322 when jaw members 310 and 320 are approximated towards one another. By varying the gaps G1, G2, and G3, end effector assembly 300 can be manufactured to accommodate different types and sizes of tissue and different cutting effects. For example, flange edge 534 may be configured to act as a stop member when jaw members 310a and 320a are approximated towards each other such that flange edge 534 grasps tissue against cutting plate 316. The flange edge 534 may be configured to create a gap of about 0.001 inches to about 0.006 inches between sealing plates 312 and 322. It is envisioned that the pressure of the tissue held therebetween may be set to a desired pressure (e.g., about 3 $kg/cm^2$ to about 16 $kg/cm^2$) to effectively seal tissue therebetween.

As can be appreciated, the various geometrical configurations and electrical arrangements of the aforementioned end effector assemblies allow the surgeon to initially activate the two opposing electrically conductive tissue contacting surfaces and seal the tissue and, subsequently, selectively and independently activate the cutting plate and one or more tissue contacting surfaces to cut the tissue utilizing the various above-described and shown end effector assembly configurations. Hence, the tissue is initially sealed and thereafter cut without re-grasping the tissue.

The cutting plate and one or more tissue contacting surfaces may also be activated to simply cut tissue/vessels without initially sealing. For example, the jaw members 310 and 320 may be positioned about tissue and the cutting plate 330 may be selectively activated to separate or simply coagulate tissue. This type of alternative embodiment may be particularly useful during certain endoscopic procedures wherein an electrosurgical pencil is typically introduced to coagulate and/or dissect tissue during the operating procedure.

As disclosed herein, the present disclosure relates to the transfer of electrosurgical energy though opposing electrically conductive cutting plates 316 and 330, each having different electrical potentials to effect vessel cutting. However, it is also contemplated that the presently disclosed embodiments, discussed herein, may be designed to cut the tissue structure using so-called "resistive heating" whereby, for example, the electrically resistive cutting plates, for example, 316 and 330, are not necessarily electrically conductive surfaces. Rather, each of the electrically resistive cutting plates 316 and 330 is heated much like a conventional "hot iron" such that the electrically resistive cutting plates 316 and 330 cooperate to cut the tissue upon contact and/or upon activation of a switch (e.g., 200 or 202) that selectively heats each electrically resistive cutting plate 316 and 330 upon activation. In this embodiment, the resistive heating is achieved using, for example, but not limited to large heating blocks, resistive heating wire, flexible foil heaters, resistance wire flexible heaters, and/or an externally heated element. In order to effectively cut tissue, the heat plates are heated to a threshold temperature of about at least 100° C.

Figure 9:
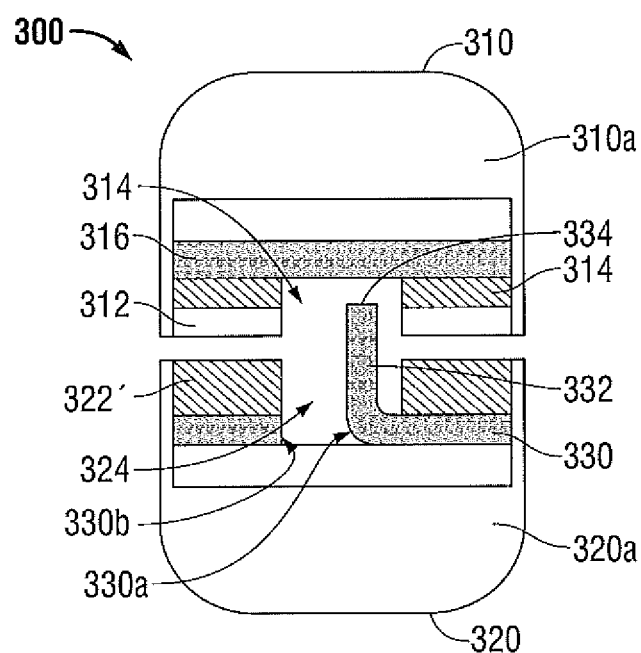
FIG. 9 is a front cross-sectional view of the end effector assembly of FIG. 6 illustrating another embodiment of tissue contacting plate in accordance with an embodiment of the present disclosure.

In another embodiment, as best shown in FIG. 9, the end effector assembly 300 includes a pair of opposing jaw members 310 and 320 and electrically conductive cutting plates 316 and 330. The pair of opposing and jaw members 310 and 320 is movable to cooperatively grasp tissue. The jaw members 310 and 320 are covered by insulating jaw covers 310a and 320a, respectively. Each of the jaw members 310 and 320 includes a tissue contacting plate 312 and 322' that is disposed thereon and has a longitudinal channel 314 and 324 that is defined therealong. The longitudinal channels 314 and 324 are disposed in substantial vertical registration relative to one another. Electrically conductive cutting plate 330 is disposed on jaw member 320 below the tissue contacting plate 322' and is adapted to connect to a first potential of an electrosurgical energy source 206 (as shown in FIG. 1). The electrically conductive cutting plate 330 includes a cutting element 332 that extends along the electrically conductive cutting plate 330 and into the longitudinal channel 324 of the jaw member 320 to engage and electrosurgically sever tissue upon activation thereof. The cutting element 332 may include a cutting edge 334 that facilitates mechanical separation of tissue during electrical activation thereof.

In this embodiment, tissue contacting plate 322' of jaw member 320 is electrically non-conductive. In this manner, the electrically conductive cutting plate 330 of jaw member 320 is sandwiched between two layers of insulative material 322' and 320a.

Figure 10:
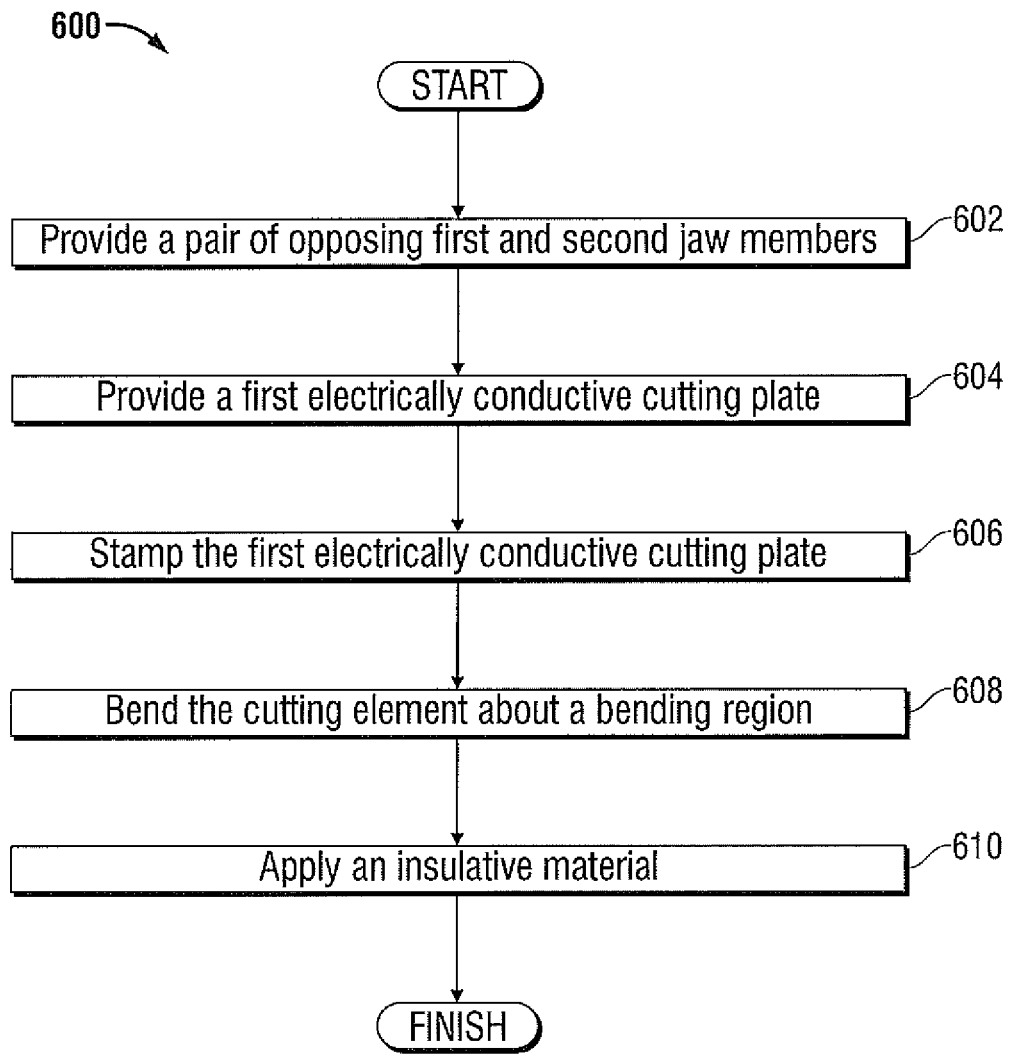
FIG. 10 illustrates a method of manufacturing an end effector assembly in accordance with an embodiment of the present disclosure.

The present disclosure also includes a method of manufacturing the end effector assembly as illustrated in the flow chart of FIG. 10. The method includes a step 602 of providing a pair of opposing jaw members 310 and 320 that is movable to cooperatively grasp tissue. Each of the jaw members 310 and 320 include a tissue contacting plate 312 and 322 that is disposed thereon and has a longitudinal channel 314 and 324 that is defined therealong. The longitudinal channels 314 and 324 are disposed in substantial vertical registration relative to one another, respectively. The method also includes a step 604 of providing and disposing an electrically conductive cutting plate 330 on the jaw member 320 below the tissue contacting plate 322. The electrically conductive cutting plate 330 is also adapted to connect to a first potential of an electrosurgical energy source 206 (as shown in FIG. 1). The method also includes a step 606 of stamping the electrically conductive cutting plate 330 to define a cutting element 332. The method also includes a step 608 of bending the cutting element 332 about a bending region 330a such that the cutting element 332 extends along the electrically conductive cutting plate 330 and into the longitudinal channels 314 and 324 of the opposing jaw members 310 and 320. The method also includes a step 610 of applying an insulative material 324a to a portion of the electrically conductive cutting plate 330.

The method 600 also includes a step of applying an insulative coating to the components that are not intended to be used for cutting. In an additional or alternative step, first and second insulating materials 314a, 314b are provided and mounted to the first and second sides of the cutting plate, while at the same time, allowing the cutting element 332 to be exposed and, thus, not insulated. In another step, a jaw cover 320a is provided and mounted on the jaw member 320 such that the cover 320a insulates any electrical current occurring around the jaw members during electrosurgical surgery. A similar method is utilized for the other jaw member 310 except the cutting plate 316 is not press-cut to include a flange. In another step, the jaw members 310 and 320 are coupled together to form an end effector assembly 300. In another step, the end effector assembly 300 is mounted and attached to a distal end of an open or endoscopic electrosurgical instrument.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An end effector assembly for use with an electrosurgical instrument, the end effector assembly comprising:
a pair of opposing first and second jaw members having a longitudinal axis defined therebetween, at least one of the first and second jaw members moveable relative to the other from a first, open position to a second, closed position for grasping tissue, each of the first and second jaw members including a tissue contacting plate disposed thereon and extending along the longitudinal axis and having a longitudinal channel defined therealong, the longitudinal channels disposed in substantial vertical registration relative to one another along the longitudinal axis; and
a first electrically conductive cutting plate disposed within the first jaw member, the cutting plate having a bent stamped portion that forms a cutting element that extends perpendicularly relative to the longitudinal axis along the first electrically conductive cutting plate and into the longitudinal channel of at least the first jaw member to engage and electrosurgically sever tissue upon activation thereof, wherein a remaining portion of the cutting plate forms a perimeter around the stamped portion, wherein the bent stamped portion extends from at least one segment of the perimeter and defines a gap between the bent stamped portion and the perimeter, and wherein the tissue contacting plate of the first jaw member is electrically conductive and adapted to connect to an electrosurgical energy source; and an insulator disposed between the tissue contacting plate and the first electrically conductive cutting plate.

2. The end effector assembly according to claim 1, wherein the tissue contacting plate of the first jaw member is electrically non-conductive.

3. The end effector assembly according to claim 1, wherein at least a portion of the electrically conductive cutting plate of the first jaw member is sandwiched between two layers of insulative material.

4. The end effector assembly according to claim 1, wherein the second jaw member includes a second electrically conductive cutting plate disposed on a non-tissue contacting side of the tissue contacting plate, the second electrically conductive cutting plate of the second jaw member adapted to connect to the electrosurgical energy source, at least a portion of the second electrically conductive cutting plate disposed within the longitudinal channel of the tissue contacting plate of the second jaw member, and wherein at least a portion of the electrically conductive cutting plates of the jaw members are each sandwiched between two layers of insulative material.

5. The end effector assembly according to claim 4, wherein the insulative material is a polymeric material.

6. The end effector assembly according to claim 1, wherein the cutting element includes a cutting edge that facilitates mechanical separation of tissue during electrical activation thereof.

7. The end effector assembly according to claim 1, wherein the second jaw member includes a second electrically conductive cutting plate disposed on a non-tissue contacting side of the tissue contacting plate, the second electrically conductive cutting plate of the second jaw member adapted to connect to the electrosurgical energy source, at least a portion of the second electrically conductive cutting plate disposed within the longitudinal channel of the tissue contacting plate of the second jaw member.

8. The end effector assembly according to claim 7 wherein the cutting element of the first electrically conductive cutting plate and the second electrically conductive cutting plate cooperate to grasp tissue therebetween.

9. The end effector assembly according to claim 1 wherein the cutting element of the first electrically conductive cutting plate is centrally disposed within the longitudinal channel of the at least the first jaw member.

10. The end effector assembly according to claim 1 wherein the cutting element of the first electrically conductive cutting plate is non-centrally disposed within the longitudinal channel of the at least the first jaw member.

11. The end effector assembly according to claim 1, wherein the tissue contacting plates of the first and second jaw members are adapted to connect to opposite potentials of an electrosurgical energy source and upon selective activation thereof cooperate to seal tissue disposed therebetween.

12. The end effector assembly according to claim 1 wherein the cutting element of the first electrically conductive cutting plate is configured to extend into the longitudinal channel of the second tissue contacting plate when the first and second jaw members are approximated.

13. An end effector assembly for use with an electrosurgical instrument, the end effector assembly comprising:
  a pair of opposing first and second jaw members having a longitudinal axis defined therebetween, at least one of the first and second jaw members moveable relative to the other from a first, open position to a second, closed position for grasping tissue, each of the first and second jaw members including a tissue contacting plate disposed thereon and extending along the longitudinal axis having a longitudinal channel defined therealong, the longitudinal channels disposed in substantial vertical registration relative to one another along the longitudinal axis; and
  at least one electrically resistive cutting plate disposed within the first jaw member, the cutting plate having a bent stamped portion that forms a cutting element that extends perpendicularly relative to the longitudinal axis along the at least one electrically resistive cutting plate and into the longitudinal channel of at least the first jaw member to engage, heat, and separate tissue upon activation thereof, wherein a remaining portion of the cutting plate forms a perimeter around the stamped portion, wherein the bent stamped portion extends from at least one segment of the perimeter and defines a gap between the bent stamped portion and the perimeter, and wherein the tissue contacting plate of the first jaw member is electrically conductive and adapted to connect to the electrosurgical energy source; and
  an insulator disposed between the tissue contacting plate of at least one of the first and second jaw members, and the at least one electrically resistive cutting plate.

14. The end effector assembly according to claim 13, wherein the at least one electrically resistive cutting plate is configured to heat tissue to a threshold temperature assuring separation of tissue.

15. An end effector assembly for use with an electrosurgical instrument, the end effector assembly comprising:
  a pair of opposing first and second jaw members having a longitudinal axis defined therebetween, at least one of the first and second jaw members moveable relative to the other from a first, open position to a second, closed position for grasping tissue, each of the first and second jaw members including a tissue contacting plate disposed thereon and extending along the longitudinal axis and having a longitudinal channel defined therealong, the tissue contacting plates having at least a tissue contacting surface and a second surface, the longitudinal channels disposed in substantial vertical registration relative to one another along the longitudinal axis;
  at least one insulating material layer disposed radially outward of at least one of the tissue contacting plates with respect to the longitudinal axis, the at least one insulating material layer having an upper surface and a lower surface, the upper surface and the second surface contacting each other; and
  a first electrically conductive cutting plate disposed within the first jaw member radially outward of the insulating material layer and contacting the lower surface, the cutting plate including a cutting element that extends perpendicularly relative to the longitudinal axis along the first electrically conductive cutting plate and into the longitudinal channel of at least the first jaw member to engage and electrosurgically sever tissue upon activation thereof, the cutting plate including a gap defined by a perimeter surrounding the cutting element, wherein the tissue contacting plate of the first jaw member is electrically conductive and adapted to connect to an electrosurgical energy source.

* * * * *